United States Patent [19]

Hagberg et al.

[11] Patent Number: 4,495,190
[45] Date of Patent: Jan. 22, 1985

[54] DERIVATIVES OF GUANINE FOR COMBATING HERPES VIRUS INFECTIONS

[75] Inventors: Curt-Erik Hagberg, Upplands Väsby; Karl N. Johansson, Enhörna; Zsuzsanna M. I. Kovacs, Järna; Göran B. Stening, Södertälje, all of Sweden

[73] Assignee: Astra Lakemedel Aktiebolag, Sodertalje, Sweden

[21] Appl. No.: 436,522

[22] Filed: Oct. 25, 1982

Related U.S. Application Data

[63] Continuation-in-part of Ser. No. 331,648, Dec. 17, 1981, abandoned.

[30] Foreign Application Priority Data

Dec. 22, 1980 [SE] Sweden .............................. 8009040

[51] Int. Cl.³ .................... A61K 31/52; C07D 473/18
[52] U.S. Cl. .................................. 514/262; 544/276; 544/277
[58] Field of Search .................. 544/276; 424/253

[56] References Cited

U.S. PATENT DOCUMENTS 4,199,574  4/1980  Schaeffer ............................ 424/200
4,423,050  12/1983  Verheyden et al. ................. 424/253
4,451,478  5/1984  Simon et al. ........................ 424/273 R

FOREIGN PATENT DOCUMENTS 2845762  4/1979  Fed. Rep. of Germany ...... 424/253
0002252  1/1972  Japan ................................. 544/277

OTHER PUBLICATIONS

Kammura, et al., Agr. Biol. Chem., 37(9), pp. 2037-2043, (1973).

Yamazari, Chem. Pharm. Bull., 17(6), pp. 1268-1270, (1969).
De Clerq, et al., J. Med. Chem., 22(5), pp. 510-513, (1979).
Pandit, et al., Chemical Abstracts, vol. 78, 58721n, (1973).
Holy, et al., Chemical Abstracts, vol. 90, 104264p, (1979).
Holy, et al., Chemical Abstracts, vol. 91, 57369k, (1979).
Hagberg, et al., Chemical Abstracts, vol. 97, 182809d, (1982).
Keller, et al., Chemical Abstracts, vol. 96, 155085n, (1982).

Primary Examiner—Donald G. Daus
Assistant Examiner—Diana G. Rivers
Attorney, Agent, or Firm—Brumbaugh, Graves, Donohue & Raymond

[57] ABSTRACT

Novel antiviral compounds of the formula

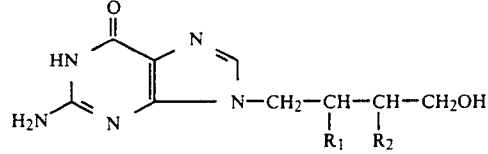

wherein each of $R_1$ and $R_2$, which are the same or different is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; or a physiologically acceptable salt or an optical isomer thereof, methods for their preparation, pharmaceutical preparations containing the compounds, and methods for the treatment of virus infections and other diseases caused by viruses.

32 Claims, No Drawings

DERIVATIVES OF GUANINE FOR COMBATING HERPES VIRUS INFECTIONS

This application is a continuation-in-part application of application Ser. No. 331,648, filed on Dec. 17, 1981, which is now abandoned.

DESCRIPTION

Field of the Invention

The present invention relates to novel derivatives of guanine, methods for their preparation, novel pharmaceutical compositions and to a method for selectively combating viruses, such as herpes viruses, etc., which can cause various diseases in animals including man. Such diseases include both common infections and neoplastic diseases, i.e. cancer.

Background of the Invention

The effects of viruses on bodily functions is the end result of changes occurring at the cellular and subcellular levels. The pathogenic changes at the cellular level are different for different combinations of viruses and host cells. While some viruses cause a general destruction (killing) of certain cells, other may transform cells to a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpesvirus group. Other important viral diseases are influenza A and B which are caused by influenza A and B virus respectively. Another important common viral disease is viral hepatitis and especially hepatitis B virus infections are widely spread. Effective and selective antiviral agents are needed for the treatment of these diseases as well as for other diseases caused by viruses. Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leucemias, sarcomas, breast carcinomas, Burkitt lymphomas, nasopharyngeal carcinomas and cervical cancers where RNA tumor viruses and herpes viruses are indicated. This makes the search for selective inhibitors of tumorogenic viruses and their functions an important undertaking in the efforts to treat cancer.

Prior Art

The compound 9-(4-hydroxybutyl)-guanine is disclosed in Chem. Pharm. Bull. 17 (1969) 1268-1270 and in Agr. Biol. Chem., 37 (1973) 2037-2043. However, no antiviral or other pharmacological activity has been disclosed for said compound.

U.S. Pat. No. 4,199,574 discloses a broad class of substituted purines of the formula

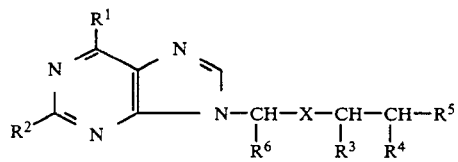

wherein X is oxygen or sulphur; $R^1$ is hydrogen, halogen, hydroxy, alkoxy, azide, thio, alkylthio, amino, alkylamino, or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl, or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate carboxypropionyloxy, straight chain or cyclic acyloxy having from 1 to 8 carbon atoms e.g., acetoxy or substituted carbamoyl group of formula NHCO-Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$ and $R^6$ are hydrogen, $R^1$ is not amino or methylamino when $R^5$ is hydrogen or hydroxy. These compounds are asserted to possess antiviral activity against various classes of DNA and RNA viruses. 9-(2-hydroxyethoxymethyl)-guanine and 2-amino-9-(2-hydroxyethoxymethyl)adenine are mentioned as examples of especially active compounds.

Disclosure of Invention

The present invention relates to the compound of the formula

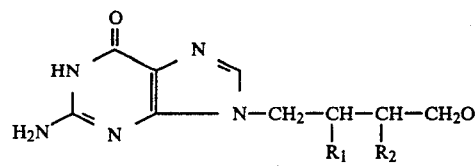

wherein each of $R_1$ and $R_2$, which are the same or different, is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; and physiologically acceptable salts or optical isomers thereof.

It has been found that such compound excerts an antiviral effect and inhibits certain viral functions including tumorogenic functions and the multiplication of viruses.

The invention thus provides a compound, and physiologically acceptable salts thereof, which compounds are useful in therapeutic and/or prophylactic treatment of viral diseases and which may be useful in therapeutic and/or prophylactic treatment of cancer caused by viruses.

An effective selective antiviral agent with acceptable side effects should have a selective inhibiting effect on a specific viral function of the virus to be combated. It is, therefore, one object of the present invention to provide a novel method for combating virus infections using an antiviral agent which exerts a selective inhibiting effect on viral functions but which exerts only a negligible inhibiting effect on functions of the host cells.

The invention also relates to novel pharmaceutical compositions containing the antiviral agents.

Although the present invention relates broadly to a novel method for combating virus infections in animals and man, and compounds to be used at such treatment, it will be particularly useful in the treatment of herpesvirus infections.

An especially important area of use for the compounds of the present invention is in the treatment of herpesvirus infections. Among the herpesviruses may be mentioned *Herpes simplex* type 1 and 2, *varicella* (*Herpes zoster*), virus causing infectious mononucleosis (i.e. Epstein-Barr virus) and cytomegalovirus. Important diseases caused by herpesviruses are herpes dermatitis, (including herpes labialis), herpes genitalis, herpes keratitis, herpes encephalitis and herpes zoster.

Another possible area of use for the compounds of the present invention are in the treatment of cancer and tumors, particularly those caused by viruses. This effect may be obtained in different ways, i.e. by inhibiting the transformation of virus-infected cells to a neoplastic state, by inhibiting the spread of viruses from transformed cells to other normal cells and by arresting the growth of virus transformed cells.

A further area of use for the compounds of the present invention is in the inhibition of transformed cells due to the presence in these cells of specific herpesvirus enzymes like thymidine kinase.

Possible areas of use for the compounds of the present invention with respect to cancer chemotherapy are treatment of leucemias, lymphomas including Burkitt lymphomas and Hodgkin's disease, sarcomas, breast carcinoma, nasopharyngeal carcinomas and cervical cancers in which viruses are indicated. Other possible areas of use for the compounds of the present invention with respect to cancer chemotherapy are treatment of multiple myeloma and cancer of the lungs (and bronchus), the stomach, the liver, the colon, the bladder, the lips, the bones, the kidneys, the ovary, the prostate, the pancreas, the skin (melanoma), the rectum, the salivary glands, the mouth, the esophagus, the testis, the brain (and cranial meninges), the thyroid gland, the gallbladder (and ducts), the nose, the larynx, connective tissues, the penis, the vulvas, the vagina, the corpus uteri and the tongue.

The invention furthermore provides

A. A method for the treatment of diseases caused by viruses in animals including man, comprising administering in an animal so infected a therapeutically effective amount of a compound of the formula I or a physiologically acceptable salt thereof.

B. A method for inhibiting the multiplication of virus, in particular herpesviruses, in animals including man, by administering to an animal in need of such treatment a compound of the formula I or a physiologically acceptable salt thereof in an amount sufficient for inhibiting said multiplication.

C. A. method for the treatment of virus-induced neoplastic diseases in animals including man, by inhibiting the growth of cells expressing viral functions, characterized by administering to an animal so infected a therapeutically effective amount of a compound of the formula I or a physiologically acceptable salt thereof.

D. A method for inhibiting the growth of virus-transformed cells in animals including man, characterized by administering to an animal in need of such treatment a compound of the formula I or a physiologically acceptable salt thereof in an amount sufficient for inhibiting said growth.

E. A method for the treatment of virus-induced neoplastic diseases in animals including man, by inhibiting the multiplication of tumor viruses, characterized by administering to an animal in need of such treatment a compound of the formula I or a physiologically acceptable salt thereof in an amount sufficient for inhibiting such multiplication.

F. A method for the treatment of neoplastic diseases in animals including man, characterized by administering to an animal a therapeutically effective amount of a compound of the formula I or a physiologically acceptable salt thereof.

The invention also relates to the use of a compound of the formula I or a physiologically acceptable salt thereof, in each of the above given methods A, B, C, D, E and F.

As stated previously the compound of the present invention has the formula

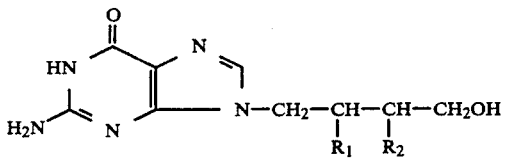

wherein each of $R_1$ and $R_2$, which are the same or different, is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; including physiologically acceptable salts and optical isomers thereof.

A preferred sub-group of compounds of the invention is obtained when at least one of the groups $R_1$ and $R_2$ in the formula I is hydroxy. Another preferred sub-group is obtained when at least one of the groups $R_1$ and $R_2$ in the formula I is fluoro.

The provisos in the definition for the groups $R_1$ and $R_2$ above mean that only the following six specific compounds, including salts and optical isomers thereof, constitute part of the present invention:
9-(3,4-dihydroxybutyl)guanine
9-(2,4-dihydroxybutyl)guanine
9-(2,3,4-trihydroxybutyl)guanine (erythro and threo).

9-(3-fluoro-4-hydroxybutyl)guanine
9-(2-fluoro-4-hydroxybutyl)guanine
9-(2,3-difluoro-4-hydroxybutyl)guanine (erythro and threo).

The first compound 9-(3,4-dihydroxybutyl)guanine is the preferred compound according to the invention.

The compounds of the formula I contain one or two asymmetric centers. Accordingly, they exist in two or four optical forms, respectively, and all such forms constitute a further aspect of the invention.

Methods of Preparation

The compounds of the invention may be obtained by one of the following methods A—X constituting a further aspect of the invention.

A. Reducing a compound of the formula $$\text{II}$$

wherein $R_1$ and $R_2$ have the meaning given above, and wherein $R^1$ is hydrogen, alkyl containing 1-8 carbon atoms, substituted or unsubstituted phenyl, or benzyl. The reduction can be carried out with borohydrides, aluminium hydrides, other hydride reducing agents, sodium in ethanol, by catalytic hydrogenation, or by similar methods known per se for the reduction of esters to alcohols. The reduction is preferably conducted in an organic solvent such as isopropanol for metal-borohydrides, dioxan for aluminium hydrides, or ethanol for catalytic hydrogenations. The reaction temperature is preferably between 0° to 50° C. for 1 hour to 3 days.

B. Hydrolysing a compound of the formula

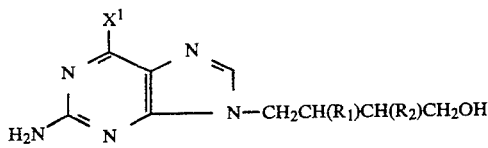

wherein $R_1$ and $R_2$ have the meaning given above, $X^1$ is a leaving group such as chlorine, bromine, iodine or a group —SH —$OR^2$, —$SR^2$ or —$SO_2R^2$ in which formulas $R^2$ is alkyl containing 1-8 carbon atoms, fluorinated alkyl containing 1-8 carbon atoms such as trifluoromethyl, or aryl such as unsubstituted or substituted phenyl.

The reaction is preferably conducted in water with an acid or base such as hydrogen chloride or sodium hydroxide at a temperature of 20° and 100° C. for 1 to 24 hours.

C1. Hydrolysing a compound of the formula

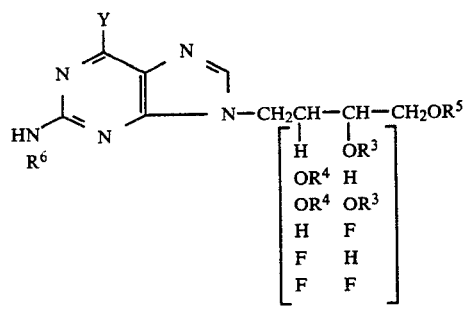

wherein Y is OH or a group $X^1$ as defined in method B, and $R^3$, $R^4$, $R^5$ and $R^6$ are the same or different and are hydrogen, —$COR^2$, or —$SO_2R^2$ wherein $R^2$ is as defined in method B.

The reaction conditions for hydrolysis are as described in method B.

C2. Hydrolysing a compound of the formula given in method C1 wherein additionally $R^3$ and $R^4$ together, or $R^3$ and $R^5$ together form a cyclic ketal as defined in method L or a cyclic carbonate ester.

The reaction conditions for hydrolysis are as described in method B.

D. Hydrolysing a compound of the formula

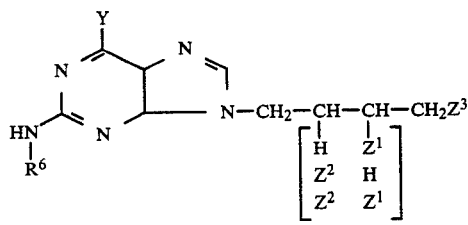

wherein Y and $R^6$ are as defined in method C and $Z^1$, $Z^2$ and $Z^3$ are the same or different and are halogen such as chlorine, bromine or iodine, or groups $OR^3$, $OR^4$ or $OR^5$ as defined in method C1 and in method C2, to the formation of a compound of the formula I wherein at least one of $R_1$ and $R_2$ is hydroxy. The reaction conditions for hydrolysis are as described in method B.

E. Hydrolysing a compound of the formula

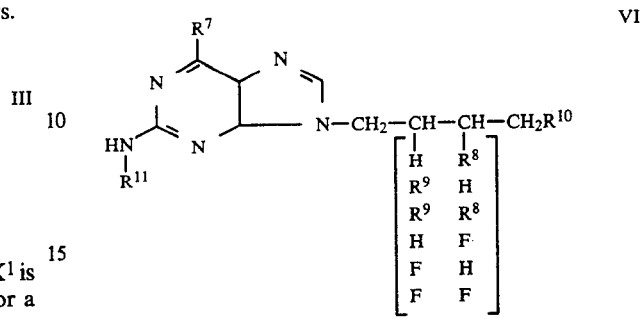

wherein $R^7$ is a silyloxy group such as trimethylsilyloxy or tert.-butyldiphenylsilyloxy or a group Y as defined in method C1, and $R^8$, $R^9$ and $R^{10}$ are the same or different and are silyl groups such as trimethylsilyloxy or tert.-butyldiphenylsilyloxy or groups $Z^1$, $Z^2$ and $Z^3$ respectively as defined in method D; and $R^{11}$ is a silyl group such as trimethylsilyl or tert.-butyldiphenylsilyl or a group $R^6$ as defined in method C.

In addition to using the reaction conditions for hydrolysis as described in method B, some silyl groups like trimethylsilyloxy may also be hydrolyzed in a solvent such as water or methanol, and other silyl groups like tert.-butyldiphenylsilyloxy may also be hydrolyzed by treatment with fluoride ion in a solvent such as pyridine at a temperature between 0° and 50° C. for 1 to 24 hours.

F. Ring-closure of a compound of the formula

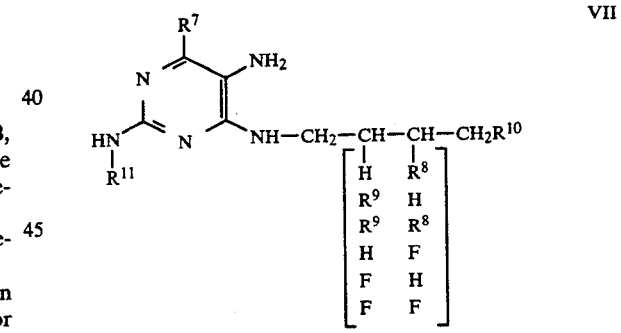

wherein $R^7$, $R^8$, $R^9$, $R^{10}$ and $R^{11}$ are as defined in method E, by reaction with formic acid or a derivate thereof such as an orthoformate ester, followed by hydrolysis of the groups $R^7$-$R^{11}$ as described in method E. The ring-closure is preferably conducted in an organic solvent such as formamide or ethanol, and at a temperature of between 20° to 210° C. for 1-10 hours.

G. Condensation of a compound of the formula

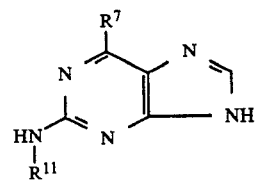

with a compound of the formula

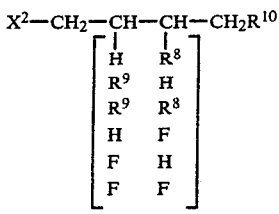   VIII wherein $R^7$–$R^{11}$ are as defined in method E and $X^2$ is a leaving group such as chlorine, bromine, iodine or a group $SO_2R^2$ where $R^2$ is defined in method B, followed by hydrolysis of the groups $R^7$–$R^{11}$ as described in method E. The condensation is preferably conducted in an organic solvent such as dimethylformamide or ethanol, and at a temperature of between 0° to 100° C. for 1 hour to 3 days, in the presence of a base such as potassium carbonate.

H. Vicinal dihydroxylation of the compound of the formula

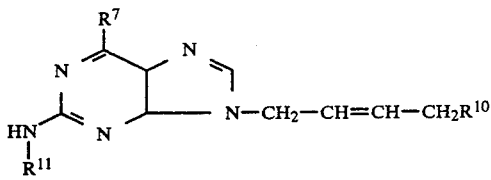   IX wherein $R^7$, $R^{10}$ and $R^{11}$ are as defined in method E, followed by hydrolysis of the groups $R^7$, $R^{10}$ and $R^{11}$ as described in method E, to the formation of a compound of the formula I wherein $R_1$ and $R_2$ are hydroxy. Dihydroxylation in a syn fashion of a cis olefin gives the erythro compound and syn addition to a trans olefin gives the threo compound. Antidihydroxylation of a cis olefin gives the threo compound and antidihydroxylation of a trans olefin gives the erythro compound. The hydroxylations may be performed by methods known per se. For example anti-hydroxylations are obtained by reagents such as hydrogen peroxide in formic acid between room temperature and 100° C. for 1 to 24 hours, by monopersuccinic acid in a solvent such as chloroform at a temperature between room temperature and 50° C. for 1 to 24 hours or by iodine and thallium- or silverbenzoate in a 1:2 molar ratio in an inert solvent such as chloroform, followed by hydrolysis of the benzoyl groups. Syn hydroxylations are obtained by using reagents such as osmiumtetraoxide, which can be used catalytically and regenerated in situ by oxidants such as aqueous sodium chlorate or oxygen in an aqueous alkaline medium at a temperature from 0° to 100° C. for 1 to 24 hours. Another reagent may be potassium-permanganate in an alkaline aqueous solution at a temperature from 0° to 50° C. for 1 to 24 hours. Syn hydroxylations can further be obtained by the addition of an acyl hypohalite, like for example $CH_3CO_2I$, which can be generated in situ in different ways, for example from silver or thallium acetate and iodine in water-acetic acid, from iodine and peracetic acid or from iodine and potassium iodate in acetic acid. The first formed β-iodo acetate can be transformed to the diol by treatment with an acetate salt like potassium or cupric acetate. The reactions are preferably conducted at a temperature between 0° and 50° C. for 1 to 24 hours.

I. Hydrolysing the compound of the formula

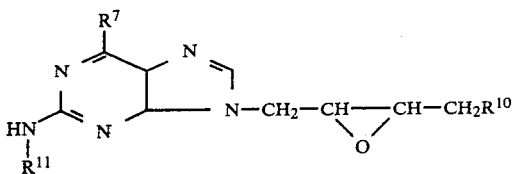   X wherein $R^7$, $R^{10}$ and $R^{11}$ are as defined in method E, to the formation of a compound of the formula I wherein $R_1$ and $R_2$ are hydroxy.

The hydrolysis of the epoxide may be performed in a solvent such as water or a mixture of water and a solvent such as dimethylformamide or ethanol. The hydrolysis is catalyzed by acids or bases such as hydrochloric acid or sodium hydroxide and is performed at a temperature of between 20° C. and 150° C. for 1 to 24 hours. The groups $R^7$, $R^{10}$ and $R^{11}$ may also be hydrolyzed as described in method E.

K. Condensation of a compound of the formula

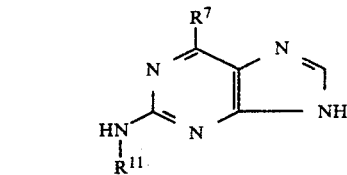   XI with a compound of the formula

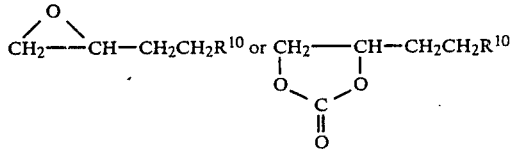

wherein $R^7$, $R^{10}$ and $R^{11}$ are as defined in method E, followed by hydrolysis of the groups $R^7$, $R^{10}$ and $R^{11}$ as described in method E, to the formation of a compound of the formula I wherein $R_1$ is hydroxy and $R_2$ is hydrogen.

The reaction conditions for condensation are for example as described in method G, or alternatively with the use of an acid catalyst.

L. Condensation of a compound of the formula

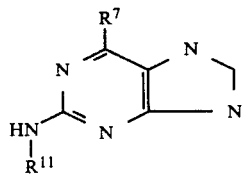

with a compound of the formula

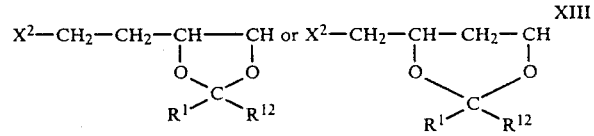   XIII in which formulas $R^1$ is as defined in method A, $R^{12}$ is alkoxy containing 1–8 carbon atoms or $R^1$; $R^7$ and $R^{11}$ are as defined in method E and $X^2$ is as defined in method G, to the formation of a compound of the formula I wherein either $R_1$ or $R_2$ is hydroxy; or a derivative thereof which can be transformed to said compound according to methods known per se.

The reaction conditions for condensation are as described in method G.

M. Reduction of a compound of the formula $$\underset{H_2N}{\overset{HN}{\diagdown}}\underset{N}{\overset{O}{\diagup}}\underset{N}{\diagdown}\text{—N—CH}_2\text{CH}_2\text{—C—COOR}^1 \qquad \text{XIV}$$

or $$\underset{H_2N}{\overset{HN}{\diagdown}}\underset{N}{\overset{O}{\diagup}}\underset{N}{\diagdown}\text{—N—CH}_2\text{—C—CH}_2\text{—COOR}^1 \qquad \text{XV}$$

wherein $R^1$ is as defined in method A, to the formation of a compound of the formula I wherein either $R_1$ or $R_2$ is hydroxy.

The reactions may be conducted under conditions such as described for method A.

N. Hydroboration of a compound of the formula $$\underset{R^{11}}{\overset{R^7}{\diagdown}}\underset{N}{\diagdown}\text{—N—CH}_2\text{CH}=\text{CH—CH}_2\text{R}^{10} \qquad \text{XVI}$$

wherein $R^7$, $R^{10}$ and $R^{11}$ are as defined in method E, followed by hydrolysis of the groups $R^7$, $R^{10}$ and $R^{11}$ as described in method E, to the formation of a mixture of the compounds of the formula I wherein either $R_1$ or $R_2$ is hydroxy. The reaction is preferably conducted with borane in an inert solvent such as tetrahydrofuran and at a temperature of between 0° and 50° C. for 1 hour to 10 hours. The formed organoborane compounds are converted to alcohols by oxidation with preferably hydrogen peroxide and sodium hydroxide in solvents such as water and tetrahydrofurane at a temperature of between 0° and 50° C. for 1 to 10 hours.

O. Reduction of a compound of the formula $$\underset{R^{11}}{\overset{R^7}{\diagdown}}\underset{N}{\diagdown}\text{—N—CH}_2\text{—C}=\text{C—CH}_2\text{R}^{10} \qquad \text{XVII}$$

$$\begin{bmatrix} H & F \\ F & H \\ F & F \end{bmatrix}$$

wherein $R^7$, $R^{10}$ and $R^{11}$ are as defined in method E, followed by hydrolysis of the groups $R^7$, $R^{10}$ and $R^{11}$ as described in method E, to the formation of a compound of the formula I wherein at least one $R_1$ and $R_2$ is fluorine.

The reduction is preferably performed with hydrogen and a catalyst such as palladium, platinum or nickel in a solvent such as ethanol and at a temperature of between 20° C. to 50° C., at a pressure of 1 to 10 atö for 1 to 48 hours.

P. Fluorination of a compound of the formula $$\underset{R^{11}}{\overset{R^7}{\diagdown}}\underset{N}{\diagdown}\text{—N—CH}_2\text{—CH—CH—CH}_2\text{R}^{10} \qquad \text{XVIII}$$

$$\begin{bmatrix} H & OH \\ OH & H \\ OH & OH \end{bmatrix}$$

wherein $R^7$, $R^{10}$ and $R^{11}$ are as defined in method E to the formation of a compound of the formula I wherein at least one of $R_1$ and $R_2$ is fluorine, or a derivative thereof which can be transformed to said compound according to methods known per se.

The fluorination is preferably conducted by reagents such as for example diethylaminosulphurtrifluoride, or diethyl-(2-chloro-1,1,2-trifluoroethyl)amine in an inert organic solvent such as chloroform or tetrahydrofuran, or by hydrogen fluoride in pyridine or triethylamine. The reaction may be performed at a temperature of between 0° and 50° C. for 1-10 hours.

R. Substitution of leaving groups $Z^1$ and/or $Z^2$ with fluorine in a compound of the formula $$\underset{H_2N}{\overset{HN}{\diagdown}}\underset{N}{\overset{O}{\diagup}}\underset{N}{\diagdown}\text{—N—CH}_2\text{—CH—CH—CH}_2\text{OH} \qquad \text{XIX}$$

$$\begin{bmatrix} H & Z^1 \\ Z^2 & H \\ Z^2 & Z^1 \end{bmatrix}$$

wherein $Z^1$ and $Z^2$ are as defined in method D, to the formation of a compound of the formula I wherein at least one of $R_1$ and $R_2$ is fluorine.

The substition may be performed with a salt such as for example potassiumfluoride, tetrabutylammoniumfluoride, polymer supported quarternary ammoniumfluoride. The substitution is preferably conducted in an inert organic solvent such as formamide, and at a temperature of between 20° to 210° C. for 0.5 to 48 hours.

S. Addition with fluorinating reagents to the isolated double bond in the compound of the formula $$\underset{R^{11}}{\overset{R^7}{\diagdown}}\underset{N}{\diagdown}\text{—N—CH}_2\text{—CH}=\text{CH—CH}_2\text{R}^{10} \qquad \text{XX}$$

wherein $R^7$, $R^{10}$ and $R^{11}$ are as defined in method E, followed by hydrolysis of the groups $R^7$, $R^{10}$ and $R^{11}$ as described in method E, to the formation of a compound of the formula I wherein at least one of $R_1$ and $R_2$ is fluorine. Addition of reagents such as fluorine, xenondifluoride and diethyl-(2-chloro-1,1,2-trifluoroethyl)amine give the difluoro compound. Addition of for example hydrogen fluoride gives the monofluoride compounds. The addition is preferably conducted in an inert organic solvent such as dioxan, and at a temperature of between 0° to 50° C. for 1 to 24 hours.

T. Hydroboration of a compound of the formula

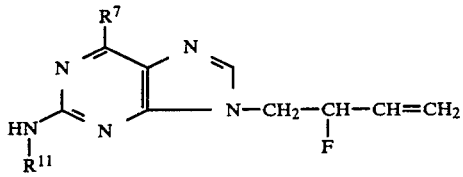  XXI wherein $R^7$ and $R^{11}$ are as defined in method E, followed by hydrolysis of the groups $R^7$ and $R^{11}$ as described in method E, to the formation of a compound of the formula I wherein $R_1$ is fluorine and $R_2$ is hydrogen.

The reaction is preferably conducted in a manner as described for method N.

U. Substitution of amino for $X^3$ in a compound of the formula

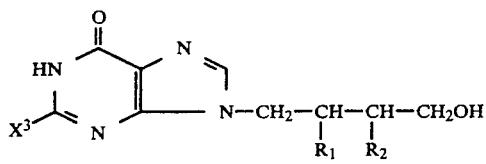  XXII wherein $R_1$ and $R_2$ have the meaning given above and $X^3$ is a leaving group such as chlorine, bromine or iodine, to the formation of a compound of the formula I.

The reaction is preferably performed with ammonia in a solvent such as methanol under super-atmospheric pressure at room temperature to 100° C. for 1 to 25 hours, or by an azide ion followed by hydrogenation using a catalyst such as for example palladium in a solvent such as ethanol at a pressure of between 0.1–1.0 MPa, and at a temperature from room temperature to 75° C. for 1 to 24 hours, or by hydrazin followed by transformation of the purine-2-hydrazinderivative to a purine-2-azide derivative with for example sodium nitrite in a solvent such as aqueous acetic acid. The azide is then hydrogenated as just described.

V. By transformation of a compound of the formula

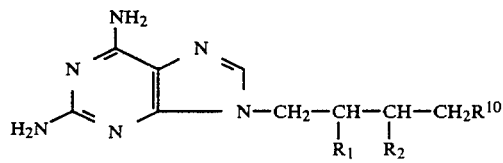  XXIII wherein $R_1$ and $R_2$ have the meaning given above and $R^{10}$ is as defined in method E, followed by hydrolysis of the group $R^{10}$ as described in method E, to the formation of a compound of the formula I, The reaction can be performed enzymatically with adenosinedeaminase in water at a pH from 6 to 9, for 1 to 48 hours, or by selective diazotization with nitrite in a solvent such as acetic acid at a temperature from room temperature to 50° C. for 1–24 hours.

W. By ring closure of a compound of the formula

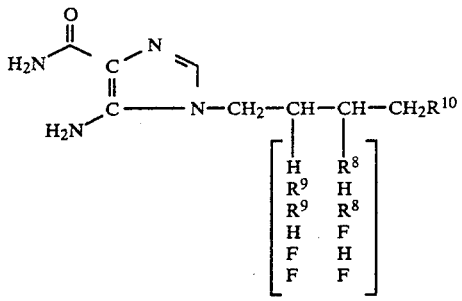  XXIV $$\begin{bmatrix} H & R^8 \\ R^9 & H \\ R^9 & R^8 \\ H & F \\ F & H \\ F & F \end{bmatrix}$$

wherein $R^8$, $R^9$ and $R^{10}$ are as defined in method E, followed by hydrolysis of the groups $R^8$, $R^9$ and $R^{10}$ as described in method E, to the formation of a compound of the formula I.

As a ring-closing reagent may be employed a reagent such as ethyl carbamate in an inert solvent such as for example dimethylformamide, at a temperature from room temperature to 150° C. for 1 hour to 24 hours, or by other ring-closures of the pyrimidine ring by known methods, as is described in for example by E. Lunt in Comprehensive Organic Chemistry, volume 4 (D. Barton and W. D. Ollis eds).

X. Hydrolysing the compound of the formula

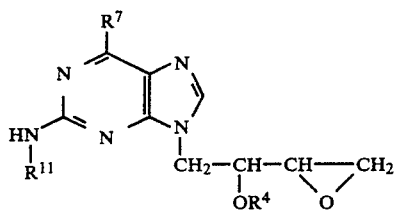  XXV wherein $R^4$ is as defined in method Cl and $R^7$ and $R^{11}$ are as defined in method E, to the formation of a compound of the formula I wherein $R_1$ and $R_2$ are hydroxy. The hydrolysis may be performed as described in method I.

The described methods A-X may be used to give enantiomeric mixtures, or in appropriate cases a single enantiomeric isomer. Additionally a single enantiomeric isomer may be obtained from the enantiomeric mixtures by methods known per se.

The starting materials in the above methods A-X are either known compounds or can be prepared according to known methods.

SALTS

Physiologically acceptable salts of compounds of the invention are prepared by methods known in the art. The salts are novel compounds and comprise a further aspect of the invention. Metal salts can be prepared by reacting a metal hydroxide with a compound of the invention. Examples of metal salts which can be prepared in this way are salts containing Li, Na, and K. A less soluble metal salt can be precipitated from a solution of a more soluble salt by addition of a suitable metal compound. Acid salts can be prepared by reacting a compound of the invention with an acid such as HCl, HBr, $H_2SO_4$, or an organic sulphonic acid.

PHARMACEUTICAL PREPARATIONS

Pharmaceutical preparation of the compounds of the invention constitute a further aspect of the invention.

In clinical practice the compounds of the invention will normally be administered topically, orally, intranasally, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. The compound may also be used without carrier material. As examples of pharmaceutical preparations may be mentioned tablets, drops, such as nasal drops, eye drops, preparations for topical application such as ointments, jellies, creams and suspensions, aerosols for inhalation, nasal spray, liposomes, etc. Usually the active substance will comprise between 0.01 and 99, or between 0.1 and 99% by weight of the preparation, for example between 0.5 and 20% for preparations intended for injection and between 0.1 and 50% for preparations intended for oral administration.

The preparations are preferably in dosage unit form. Further, they are preferably provided in sterilized form.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragées. If the dragées are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol and a plasticizer, or similar closed capsules, the active substance may be admixed with a Carbovax ® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as physiologically inert plastic substance.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution of the active drug or a physiologically acceptable salt thereof, desirably in a concentration of 0.05–10%, and optionally also a stabilizing agent and/or buffer substances in aqueous solution. Dosage units of the solution may advantageously be enclosed in ampoules.

For topical application, especially for the treatment of herpesvirus infections on skin, genitals and in mouth and eyes the preparations are suitably in the form of a solution, ointment, gel, suspension, cream or the like. The amount of active substance may vary, for example between 0.05–20% by weight of the active substance. Such preparations for topical application may be prepared in known manner by mixing the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are e.g. dimethylacetamide (U.S. Pat. No. 3,472,931), trichloroethanol or trifluoroethanol (U.S. Pat. No. 3,891,757), certain alcohols and mixtures thereof (British Pat. No. 1,001,949).

The dosage at which the active ingredients are administered may vary within a wide range and will depend on various factors such as for example the severity of the invention, the age of the patient, etc., and may have to be individually adjusted. As a possible range for the amount of the compounds of the invention which may be administered per day may be mentioned from about 0.1 mg to about 2000 mg or from about 1 mg to about 2000 mg, or preferably from 1 mg to about 2000 mg for topical administration, from 50 mg to about 2000 mg or from 100 to about 1000 mg for oral administration and from 10 mg to about 2000 mg or from 50 to about 500 mg for injection.

In severe cases it may be necessary to increase these doses 5-fold to 10-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that the compounds of the formula I and the physiologically acceptable salts thereof can be used to inhibit herpesvirus multiplication. The compounds of the formula I and physiologically acceptable salts thereof are useful in therapeutic and/or prophylactic treatment of virus infections.

A preferred aspect of the invention is the use of the compounds of the formula I or a physiologically acceptable salt thereof, in the treatment of herpesvirus infections.

WORKING EXAMPLES

The following examples illustrates the preparation of compounds according to the invention.

I. Preparation of starting materials

Example 1

Preparation of 4-bromo-2-hydroxybutyric acid ethyl ester

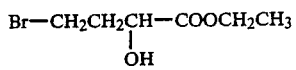

2-hydroxybutyrolactone, Brit. Pat. No. 688.253 [C A 48, p.3996 (1954)], (5.1 g) was dissolved in 10 ml ethanol and the solution was saturated with hydrogenbromide at 0° C. After standing at room temperature during 66 hours, the solvent was evaporated at a low pressure. The residue was mixed with ice-water and the mixture neutralized with 10% aqueous sodium carbonate. The mixture was then extracted several times with diethyl ether and the combined ether extracts washed with saturated, aqueous sodium sulphate and dried over anhydrous sodium sulphate. After evaporation of the solvent, the residue was distilled at 12 mm Hg. The fraction boiling at 109°–112° C. weighing 3,79 g was used in example 2 below.

Example 2

Preparation of 4-(2-amino-6-chloropurin-9-yl)-2-hydroxybutyric acid ethyl ester

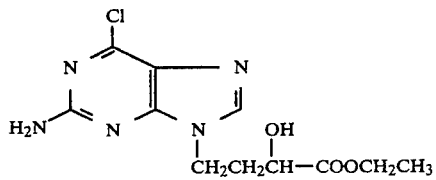

2-Amino-6-chloropurine (0.509 g, 3.00 mmole), 4-bromo-2-hydroxybutyric acid ethyl ester (0.633 g, 3.00 mmole; prepared according to Example 1) and anhydrous potassium carbonate (0.415 g, 3.00 mmole) were mixed with 10 g of dimethyl formamide and the mixture stirred at room temperature during 65 hours. The mixture was then filtered and the filtrate evaporated at a pressure of 0.1 mm Hg. The crystalline residue was triturated with 8 ml of chloroform and the undissolved material filtered off and washed with 2 ml of chloroform. The material obtained was then triturated with 5 ml of water and the undissolved material filtered off and washed with 2 ml of water. Recrystallization from 11 ml of ethanol gave 0.360 g product. M.P. 163°–4° C. (uncorr.) UV spectra(ethanol): $\lambda_{max}$(nm) 311, 248. Analyses—Found: C 43.90; H 4.78; Cl 11.72; N 23.52; O 15.90%. Calculated for $C_{11}H_{14}ClN_5O_3$: C 44.08; H 4.71; Cl 11.83; N 23.37; O 16.01%.

Example 3

Preparation of 4-(2-amino-1,6-dihydro-6-oxopurin-9-yl)-2-hydroxybutyric acid

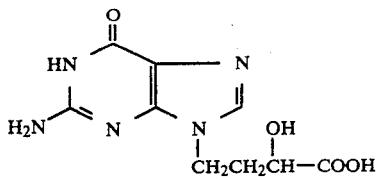

4-(2-Amino-6-chloropurin-9-yl)-2-hydroxybutyric acid ethyl ester (1.40 g, 4.67 mmole; prepared according to Example 2) in 100 ml of 1M aqueous hydrochloric acid was refluxed during 2.5 h. The solution was then evaporated at a pressure of about 10 mm Hg. Water (25 ml) was added to the residue and the solution evaporated again. This procedure was repeated 4 times. The residue was triturated with 150 ml of acetone and the semi-solid material filtered off to yield 1.38 g. This crude product (1.27 g) was partly dissolved in 5 ml of water, the solution was filtered and the undissolved material washed with 2.5 ml water. The pH of the filtrate was then adjusted to 6–7 with solid sodium bicarbonate. The water solution obtained was filtered and undissolved material washed with 7.5 ml water. 0.4 ml of acetic acid was then added to the filtrate. After cooling to 0° C., the precipitate was filtered off and washed with 3 ml of water. Recrystallization from 75 ml of water gave 0.68 g product. M.p. >250° C. (dec.). UV spectra (0.1M hydrochloric acid): $\lambda_{max}$(nm) 279, 254; UV spectra (0.1M sodium hydroxide): $\lambda_{max}$(nm) 269, 256 (infl.) Analyses—Found: C 42.63; H 4.41; N 27.74; O 25.30%. Calculated for $C_9H_{11}N_5O_4$: C 42.69; H 4.38; N 27.66; O 25.27.

Example 4

Preparation of 4-(2-amino-1,6-dihydro-6-oxopurin-9-yl)-2-hydroxybutyric acid ethyl ester

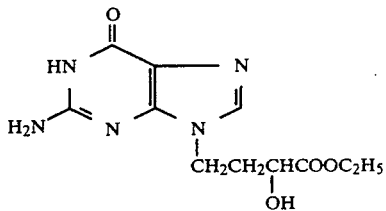

4-(2-Amino-1,6-dihydro-6-oxopurin-9-yl)-2-hydroxybutyric acid (2.00 g, 7.9 mmole; prepared according to Example 3) was mixed with 500 ml of ethanol. The mixture was saturated with hydrogen chloride gas, first without cooling and then with cooling in ice-water. The total addition time was about 15 minutes. The mixture was then slowly warmed to room temperature and allowed to stand over night. After evaporation of the solvent, the residue was treated three times each with 25 ml of ethanol, the solvent being reevaporated after each treatment. The residue was then dissolved in 12 ml of water and the pH adjusted to 6–7 with saturated aqueous sodium bicarbonate. The precipitate was filtered off, washed with 2 ml of water and dried in vacuo to yield 1.60 g. Recrystallization from ethanol gave a pure product, m.p. 161°–3° C. (a sample for analysis had m.p. 162°–3° C.). Analyses—Found: C 46.96; H 5.35; N 24.77; O 22.60%. Calculated for $C_{11}H_{15}N_5O_4$: C 46.97; H 5.38; N 24.90; O 22.75%.

Example 5

Preparation of 4-(2-amino-6-chloropurin-9-yl)methyl-1,3-dioxane

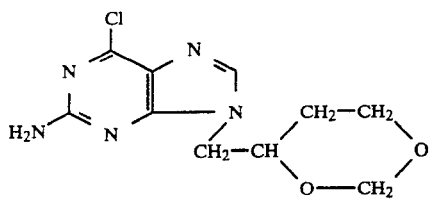

Equimolar amounts of 2-amino-6-chloropurine, 4-bromoethyl-1,3-dioxane (prepared according to Price C. C. J. Amer. Chem. Soc. 1950, 72, 5335–6) and anhydrous potassium carbonate were mixed in dry dimethyl formamide. After stirring for seven days at room temperature the mixture was filtered and the filtrate evaporated at reduced pressure. The residue was triturated with hot ethanol and undissolved material filtered off. The filtrate was evaporated to dryness and a yellow crystalline solid was obtained which was recrystallized from chloroform to give colourless rod-shaped crystals. M.p. 169°–70° C. (uncorr.) UV Spectra (hydrochloric acid 0.01 mol/l): $\lambda_{max}$(nm) 308, 245. UV spectra (ethanol): $\lambda_{max}$(nm) 310, 247. M.S.: 11.2 a J., m/e (int): 271/269 (0.19/0.55), 226/224 (0.11/0.28) 212/210 (0.38/0.82) 171/169 (0.35/1.0)

Example 6

Preparation of 2-fluorobutyrolactone

2-Bromobutyrolactone (15 g) and silverfluoride (23 g) were stirred for 24 hours in refluxing, dry acetonitrile (150 ml). After cooling to room temperature the mixture was filtered and the solvent was evaporated in vacuo. The dark residue was dissolved in ethyl acetete (200 ml) and washed with water (6×50 ml). The water phase was backwashed with ethyl acetate (80 ml) and the combined ethyl acetate solution was dried over $MgSO_4$ and evaporated to give 2-fluorobutyrolacetone (21%). $^1$H-NMR (acetone-$d_6$, Me$_4$Si): $\delta$5.02 and 5.95 for CHF (two triplets, J=8 Hz. $J_{CHF}$=51 Hz).

Example 7

Preparation for 4-bromo-2-fluorobutyric acid ethyl ester

Hydrogen bromide gas was added over a period of about 30 minutes to a solution of 2-fluorobutyrolactone (1.8 g) in ethanol (15 ml) at 0° C. The reaction mixture was left at room temperature for 3 days, after which it was evaporated in vacuo. The residue was dissolved in icewater, the solution was neutralized with sodiumcarbonate and extracted with ether. The ether solution was washed with an aqueous saturated $Na_2SO_4$ solution, dried over $Na_2SO_4$ and evaporated to give 4-bromo-2-fluorobutyric acid ethyl ester (1.26 g, 34%). $n_D^{20}$=1.4698. $^1$H-NMR (CDCl$_3$, MeSi)$\delta$: 1.3 (t, J=7 Hz, CH$_3$); 2.1–2.8 (m, CH$_2$); 3.55 (t, J=7 Hz, CH$_2$Br); 4.3 (q, J=7 Hz, CH$_2$); 4.75 and 5.55 (two triplets, J=6 Hz, CHF, $J_{CHF}$=50 Hz).

Example 8

Preparation of 4-(2-amino-6-chloropurin-9-yl)-2-fluorobutyric acid ethyl ester

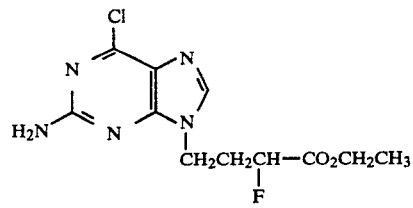

4-Bromo-2-fluorobutyric acid ethyl ester (0.23 g), 2-amino-6-chloropurine (0.19 g) and anhydrous potassium carbonate (0.15 g) were mixed and stirred in dimethylformamide (3.7 ml) at room temperature for two days. The solution was filtered and evaporated in vacuo. The residue was triturated with chloroform (4+2 ml) and the clear chloroform solution was evaporated to give the desired product (0.24 g, 72%). TLC (silica gel, i-propanol-water-conc. ammonia 8-1-1): $R_f$=0.76. NMR (CDCl$_3$, Me$_4$Si)$\delta$: 1.26 (t, CH$_3$); 2.4–2.5 (m, CH$_2$); 4.2–4.3 (t and q, NCH$_2$ and CO$_2$CH$_2$); 4.77 and 5.03 (CHF, J=51 Hz); 5.2 (NH$_2$); 7.77 (8-CH).

Example 8

Preparation of 4-(2-amino-6-chloropurin-9-yl)-2-fluorobutanol

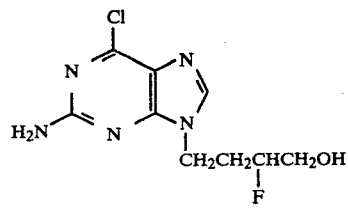

Sodium borohyride (15 mg) was dissolved in dry diethyleneglycoldiethylether (0.9 ml) and stirred. Finely powdered and dry lithiumbromide (34 mg) was added, followed after ½ hour by 4-(2-amino-6-chloropurin-9-yl)-2-fluorobutyric acid ethyl ester (100 mg). The reaction mixture was heated at 100° C. for 3 hours, then poured onto crushed ice (10 g) with added concentrated hydrochloric acid (0.5 ml) and stirred. The pH was adjusted to 6.5 by sodium hydrogen carbonate, the solution was evaporated in vacuo and the residue was redissolved in methanol-chloroform (40–60, 10 ml) and filtered. The solution was purified by chromatography on a silica gel column eluted with a methanol-chloroform gradient, to give the desired product (52 mg, 60%) TLC (silica gel, methanol-chloroform 40–60): $R_f$=0.66. UV (ethanol)$\lambda_{max}$: 310 and 247 nm.

II Preparation of compounds of the invention

Example 10

Preparation of 9-(3,4-dihydroxybutyl)guanine

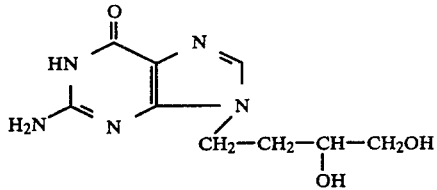
(VIS 707)

To a suspension of ethyl 4-(2-amino-1,6-dihydro-6-oxopurin-9-yl)-2-hydroxybutyrate (prepared according to Example 4) in iso-propanol was added an excess of sodium borohydride and the mixture was refluxed over night (at least 8 hours). Hydrochloric acid was added until a clear solution was obtained (neutral pH). After removal of the solvent the residue was dissolved in a minimum amount of boiling water and kept at 0° C. for a couple of hours. The solid was filtered off. The filtrate was evaporated at reduced pressure and the residue dissolved in hydrochloric acid (1 mol/l) and adsorbed on a cation exchange resin (Dowex 50 W, $H^+$-form). The resin was washed with water and then eluted with 5% ammonium hydroxide. The eluent was evaporated to give a crystalline solid which was recrystallized from water to afford colourless needles. M.p. 260°-1° C. (dec.) (uncorrected) UV spectra (hydrochloric acid 0.01 mol/l): $\lambda_{max}$(nm) 277, 253 ($\epsilon$=11500) M.S: 11.2 a J. (int): 239 ($M^+$, 0.13), 222 (0.19), 221 (0.11), 152 (0.43), 151 (0.56), 44 (1.0).

Example 11

Preparation of 9-(2,4-dihydroxybutyl)guanine

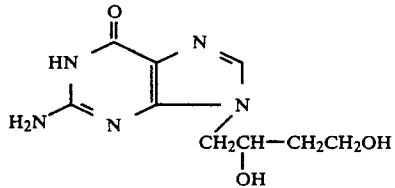
(VIS 715)

4-(2-amino-6-chloropurin-9-yl)methyl-1,3-dioxane (prepared according to Example 5) was dissolved in hydrochloric acid (1 mol/l) and refluxed for four hours. The solution was made alkaline with diluted ammonium hydroxide and evaporated to dryness at reduced pressure. The residue was dissolved in water and purified with preparative HPLC on a reversed phase column ($\mu$ Bondapack $C_{18}$)eluted with a mixture of methanol and water (1:3). The product obtained was a white crystalline solid. M.p. 226°-8° C. (dec) (uncorrected) UV spectra (hydrochloric acid 0.01 mol/l): $\lambda_{max}$(nm) 277, 254 ($\epsilon$=10700).

Example 12

Preparation of 9-(3-fluoro-4-hydroxybutyl)guanine

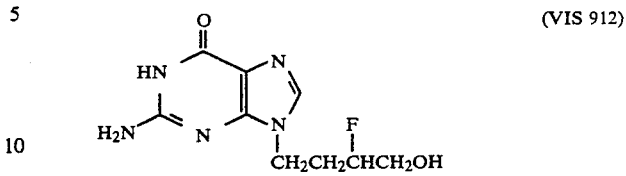
(VIS 912)

4-(2-amino-6-chloropurin-9-yl)-2-fluorobutanol (52 mg) was heated in refluxing 1M aqueous HCl (4.5 ml) for 50 minutes. The solution was evaporated in vacuo, the residue was redissolved in water, and the solution was neutralized with 1M ammonia and lyophilized. The residue was purified over an anion exchange column (Dowex 1×2, $OH^-$). The evaporated solution gave the desired product (37 mg, 77%). NMR (DMSO-$d_6$)$\delta$: 1.95-2.15 (m, $CH_2$); 3.3-3.5 (m, $CH_2O$); 4.05 (t, $NCH_2$); 4.3 and 4.5 (CHF, J=49 Hz); 6.45 ($NH_2$); 7.7 (8-CH); 10.6 (NH).

Example 13

Preparation of 9-(DL-erythro-2,3,4-Trihydroxybutyl) guanine

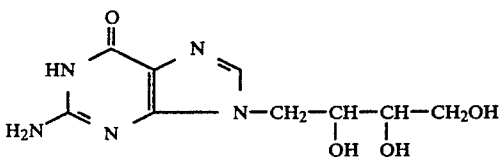
(VIS 925)

6-Chloroguanine (0.75 g) and sodium hydride (60% in oil, 0.18 g) in dry dimethylformamide were stirred at room temperature for one hour. DL-erythro-2,2-Dimethyl-4-p-toluenesulfonyloxymethyl-5-hydroxymethyl-1,3-dioxolane [0.70 g, prepared according to A. Hol, Coll. Czech. Chem. Commun Vol 44, pages 593-612 (1979)] was added and the reaction mixture was heated at 100° C. for 17 hours, after which it was filtered through a Celite pad, and the solution was evaporated in vacuo. The residue was refluxed with acetic acid (25 ml) for 2 hours. The solvent was evaporated and the residue was coevaporated with water (3×5 ml). The residue was dissolved in a small volume of 1N hydrochloric acid, and added to a column of Dowex 50×8 ($H^+$, 70 ml)which was eluted with water (1 liter) followed by aqueous ammonia (diluted 1/10). The elution was monitored by a UV detector. The appropriate fractions were evaporated in vacuo, and the residue was coevaporated with water several times, finally dissolved in boiling water (230 ml) and filtered to give 9-(DL-erythro-2,3,4-trihydroxybutyl) guanine (0.20 g). NMR (DMSO-$d_6$)$\delta$: 7,8 (s,8C-H); 6.4 ($NH_2$); 4.22 (N-$CH_2$).

Example 14

Preparation of R-(+)-9-(3,4-di-hydroxybutyl) guanine

Step a: Preparation of R-(+)-1,2,4 butantriol.

R-(+)-Dimethyl malate (1.62, 10 mmol), prepared according to Boger, D. L. and Panek, J. S., J. Org. Chem. 1981, 46, 1208-10, was dissolved in THF (10 ml) and added dropwise to a prewarmed suspension of lithium aluminium hydride (0.63 g, 16.5 mmol) in THF (15 ml). The reaction mixture was stirred over night at 55° C. After sequential addition of water (0.62 ml), 10% sodium hydroxide (1.20 ml) and water (1.90 ml) the mixture was filtered and the solid residue was boiled twice with THF (2×20 ml) and filtered. The combined filtrates were pooled and evaporated under reduced pressure (13 Pa, 30° C.) leaving crude 1,2,4-butantriol (0.7 g, 6.6 mmol) 66%.

Step b: Preparation of R-(+)-isopropylidenbutan 1,2,4 triol.

R-(+)-1,2,4-butantriol (0.7 g, 6.6 mmol), prepared as described in step (a) above, was stirred for 1.5 hr in acetone (50 ml) containing 3 drops of conc. perchloric acid a satured solution of sodium bicarbonate in water (5 ml) was added and the stirring was continued for additional 10 min. The precipitate was filtered off and the filtrate evaporated under reduced pressure (2.7 kPa, 30° C.). The residue was taken up in ethyl acetate, washed with satured aqueous sodium bicarbonate (5 ml) and brine (5 ml), and dried over magnesium sulphate. Evaporation of the solvent and distillation gave the title compound as a colourless oil (0.3 g, 2.05 mmol, 31%): b.p. 104°-6° C. at ≈2.7 kPa. $n_D^{20}=1.4390$.

Step c: Preparation of R-(+)-4-bromo-isopropylidenebutan-1,2 diol.

R-(+)-isopropylidene-butan-1,2,4 triol (0.3 g, 2.05 mmol) and triphenylphosphine (0.63 g, 2.4 mmol) was dissolved in methylene chloride (5 ml) and cooled to 0° C. N-bromosuccinimide (0.38 g, 2.16 mmol) was added in small portions with stirring at 0° C. After additional 1 hr of stirring at 0° C. hexane (15 ml) was added and the resulting precipitate was removed by filtration and washed twice with hexane (2×5 ml). The combined hexane solution was passed through a short column of silica gel (5 g). Elution with hexane (15 ml) gave after evaporation and distillation the title compound as a colourless oil (0.2 g, 0.96 mmol, 47%): b.p. 74–6 at 2.7 kPa (20 mm Hg), $n_D^{20}=1.4630$. $[\alpha]_D^{20}=+27.7$ (C=20, CHCl$_3$).

Step d: Preparation of R(+)-4-(2-amino-6-chloropurin-9-yl)isopropylidene-butane-1,2 diol.

2-amino-6-chloropurin (162 mg, 0.96 mmol), R(+)-4-bromo-isopropylidene-butandiol (200 mg, 0.96 mmol) and potassium carbonate (132 mg) was mixed in DMF (10 ml). After stirring for 16 hr the reaction mixture was filtered through celite and the solvent evaporated under reduced pressure [13 Pa (0.1 mm Hg), 50° C.]. The residue was triturated with warm chloroform (5 ml) and undissolved material was filtered off. Evaporation of the solvent gave a pale yellow crystalline solid consisting mainly of the 9- and 7-isomers. These were separated by silica gel flash chromatography. Elution with chloroform/methanol (15:1) gave the title compound in pure form (106 mg, 0.36 mmol, 37%): m.p. 129°-30° C., $[\alpha]_D^{21}=+57.5$ (C=6.97, CHCl$_3$).

Step e: Preparation of R-(+)-9-(3,4-dihydroxybutyl) guanine.

R(+)-4-(2-amino-6-chloropurin-9-yl)isopropylidenebutane-1,2 diol (100 mg, 0.33 mmol) prepared according to step (d) above was dissolved in hydrochloric acid (1 mol/l) and refluxed for 1 hr. The solution was concentrated in vacuum and the residue dissolved in water (5 ml) and made alkaline by addition of aqueous ammonium hydroxide. After evaporation the solid residue was recrystallized from water giving the title compound as white needles (40 mg, 0.17 mmol, 51%). UV spectra (hydrochloric acid 0.01 mol/l $\lambda_{max}$(nm)277, 253. $[\alpha]_D^{21}=+30.8$ (C=0.25, water). PMR (D$_2$O ref. int. t-BuOH, $\delta_{CH3}=1.23$ ppm), 1.75–2.15 ppm (m, 2H), 3.40–3.70 ppm (m, 3H), 4.15 ppm (ABq, 2H) and 7.77 ppm (S, 1H).

The following examples illustrate the preparation of pharmaceutical compositions of the invention. The wording "active substance" denotes a compound according to the present invention or a salt thereof, and preferably the compound 9-(3,4-dihydroxybutyl)-guanine.

Example 15

Tablets

Each tablet contains:

| | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

Example 16

Suppositories

Each suppository contains:

| | |
|---|---|
| Active substance | 20.0 mg |
| Ascorbyl palmitate | 1.0 mg |
| Suppository base (Imhausen H or Witepsol ® H) | ad 2000.0 mg |

Example 17

Syrup

| | |
|---|---|
| Active substance | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

Example 18

Injection solution

| | |
|---|---|
| Active substance | 3.000 mg |
| Sodium pyrosulfite | 0.500 mg |
| Disodium edetate | 0.100 mg |
| Sodium chloride | 8.500 mg |
| Sterile water for injection | ad 1.00 ml |

Example 19

Sublingual tablets

| | |
|---|---|
| Active substance | 5.0 mg |
| Lactose | 85.0 mg |
| Talc | 5.0 mg |
| Agar | 5.0 mg |

Example 20

Jelly

| | |
|---|---|
| Active substance | 1.0 g |
| Methocel ® | 4.0 g |
| Methyl paraoxybenzoate | 0.12 g |
| Propyl paraoxybenzoate | 0.05 g |
| Sodium hydroxide and hydrochloric acid to pH 6.7 | |
| Distilled water | ad 100.0 ml |

Example 21

Ointment I

| | |
|---|---|
| Active substance | 1.0 g |
| Cetyltrimethylammoniumbromide | 0.6 g |
| Stearyl alcohol | 2.25 g |
| Cetanol | 6.75 g |
| Liquid paraffine | 17.0 g |
| Glycerol | 12.0 g |
| Hydrochloric acid to pH 6.5 | |
| Distilled water | ad 100.0 g |

Example 22

Ointment II

| | |
|---|---|
| Active substance | 3.0 g |
| Polyethylene glycol 1500 | 50 g |
| Polyethylene glycol 4000 | 15 g |
| Propylene glycol | ad 100 g |

Example 23

Ointment III

| | |
|---|---|
| Active substance | 3.0 g |
| Sorbitan monoleate | 5.0 g |
| Petrolatum | ad 100 g |

Example 24

Ointment IV

| | |
|---|---|
| Active substance | 5 g |
| Adeps lane | 20 g |
| Tween ® 60 | 4 g |
| Span ® 40 | 2 g |
| Paraffin, liquid | 4 g |
| Propylene glycol | 5 g |
| Hydrochloric acid to pH 6.5-8 | |
| Sterile water | ad 100 g |

Example 25

Ointment V

| | |
|---|---|
| Active substance | 5 g |
| Adeps lane | 20 g |
| Tween ® 60 | 4 g |
| Span ® 40 | 2 g |
| Paraffin, liquid | 4 g |
| Propylene glycol | 5 g |
| Boric acid | 2 g |
| Sodium hydroxide to pH 6.5-8 | |
| Sterile water | ad 100 g |

Example 26

Eye drops I

| | |
|---|---|
| Active substance | 0.1 g |
| Disodium edetate | 0.10 g |
| Sodium chloride for isotonia q.s. | |
| Hydrochloric acid to pH 6.5-8 | |
| Methocel ® 65 HG 4000 | 0.65 |
| Sterile water | ad 100 ml |

Example 27

Eye drops II

| | |
|---|---|
| Active substance | 0.3 g |
| Disodium edetate | 0.10 g |
| Sodium chloride for isotonia q.s. | |
| Hydrochloric acid to pH 6.5-8.0 | |
| Methocel ® 65 HG 4000 | 0.65 |
| Sterile water | ad 100 ml |

Example 28

Eye drops III

| | |
|---|---|
| Active substance | 0.2 g |
| Disodium edetate | 0.1 g |
| Sodium chloride for isotonia q.s. | |
| Boric acid | 0.1 g |
| Methocel ® 65 HG 4000 | 0.65 g |
| Sterile water | ad 100 ml |

Example 29

Eye ointment I

| | |
|---|---|
| Active substance | 3 g |
| Paraffin oil | 19 g |
| Petrolatum | 78 g |

Example 30

Cream

| | |
|---|---|
| Active substance | 3.0 g |
| Arlaton ® | 4.0 g |
| Cetanol | 2.0 g |
| Stearic acid | 2.0 g |
| Paraffin oil | 2.0 g |
| Propylene glycol | 2.0 g |
| Glycerol | 1.5 g |
| Methyl-p-hydroxybenzoate | 0.06 g |
| Propyl-p-hydroxybenzoate | 0.03 g |
| Sodium hydroxide | 0.002 g |
| Hydrochloric acid 2M to pH 8.0 (water phase) | |
| Distilled water | to 100 g |

Example 31

Jelly

| | |
|---|---|
| Active substance | 3.0 g |
| Methocel ® | 2.45 g |
| Glycerol | 10.0 g |
| Tween ® | 0.10 g |
| Methyl-p-hydroxybenzoate | 0.06 g |
| Propyl-p-hydroxybenzoate | 0.03 g |
| Sodium hydroxide | 0.002 g |
| Hydrochloric acid 2M to pH 8.0 | |
| Distilled water | to 100 g |

Example 32

Tablets

Each tablet contains:

| | |
|---|---|
| Active substance | 100.0 mg |
| Starch | 60.0 mg |
| Lactose | 190.0 mg |
| Polyvinylpyrrolidone | 5.0 mg |
| Magnesium stearate | 5.0 mg |
| | 360.0 mg |

BIOLOGICAL TESTS

The inhibiting effect of compounds of the invention on herpesvirus was tested using the methods described below. The cellular toxicity of the compounds on host cell functions was also tested.

In the following the compound 9-(3,4-dihydroxybutyl)guanine (base) is denoted VIS 707, the compound 9-(2,4-dihydroxybutyl)guanine (base) is denoted VIS 715, and the compound 9-(3-fluoro-4-hydroxybutyl)guanine (base) is denoted VIS 912.

I. Inhibition of virus multiplication in cell cultures

The inhibition of herpesvirus by VIS 707, VIS 715 and VIS 912 has been measured as plaque reduction according to the following procedure.

A. Inhibition by VIS 707, VIS 715 and VIS 912 of herpes simplex type 1 plaque The plaque reduction, assay for herpes simplex type 1 was performed on Vero (Green Monkey Kidney) cells as described by Ejercito et al., J. Gen. Virol. 2 (1968) 357. Monolayers on 5 cm petri dishes were used and after virus adsorption the compounds to be tested VIS 707, VIS 715 or VIS 912 were added in the medium. The results are shown in table 1.

TABLE 1

Inhibition by VIS 707, VIS 715, and VIS 912 of herpes simplex type 1 plaque on Vero cell monolayers

| Conc. ($\mu$M) | Compound | Inhibition (%) |
|---|---|---|
| 1 | (VIS 707) | 65 |
| 5 | (VIS 707) | >90 |
| 100 | (VIS 715) | 90 |
| 10 | (VIS 912) | 30 |
| 50 | (VIS 912) | 85 |
| 100 | (VIS 912) | >90 |

B. Inhibition by VIS 707 and VIS 912 of herpes simplex type 2 plaque

The plaque reduction assay for herpes simplex type 2 was performed in the same way as in experiment A. The results are shown in table 2.

TABLE 2

Inhibition by VIS 707 and VIS 912 of herpes simplex type 2 patient isolate plaque on Vero cell monolayers

| Conc. ($\mu$M) | Compound | Inhibition (%) |
|---|---|---|
| 10 | (VIS 707) | 85 |
| 20 | (VIS 707) | >99 |
| 100 | (VIS 707) | 100 |
| 100 | (VIS 912) | 80 |

II. Cellular toxicity

VIS 707, VIS 715 and VIS 912 were tested for cellular toxicity as shown in Table 3. The method used has been described by Stenberg (Biochemical Pharmacology, in press). It is seen that VIS 707 did not significantly affect cell growth at 100 $\mu$M. However, at the much lower concentration of 5 $\mu$M, herpes virus multiplication was inhibited to more than 90% (see Table 1).

TABLE 3

Cellular toxicity of VIS 707, VIS 715 and VIS 912, expressed as percent reduction in cell growth after 48 h of incubation

| Conc. ($\mu$M) | Compound | Percent reduction in growth of Vero cells, determined as cell number |
|---|---|---|
| 100 | (VIS 707) | 10 |
| 100 | (VIS 715) | 29 |
| 100 | (VIS 912) | 30 |

III. Animal experiments

A. Experiments on herpes keratitis in rabbits have shown that VIS 707 in topical preparations according to Example 28 has a therapeutic effect. The method used has been described by Alenius et al (Acta Ophthalmologica Vol. 58 (1980) 167–173). Treatment started 3 days after infection and continued for 5 days. All treatments were given four times daily. The results are shown in Table 4, wherein 0 represents normal cornea and 3 represents extensive corneal ulceration.

TABLE 4

Effect of 3% VIS 707 ointment on superficial keratitis in rabbits

| | Day: | | | | |
|---|---|---|---|---|---|
| | 3 | 5 | 7 | 10 | 12 |
| | Severity of keratitis | | | | |
| 3% VIS 707 ointment | 1.0 | 0.75 | 0 | 0 | 0 |
| Placebo ointment | 0.6 | 1.6 | 2.5 | 0.4 | 0.6 |

B. Experiments on cutaneous herpes in guinea pigs have shown that VIS 707 in topical preparations according to Example 22 has a therapeutic effect. The method used has been described by Alenius et al (Archives of Virology 58 (1978) 277–288). Treatment started 24 hours after infection and continued for 4 days. All treatments were give four times daily. The results are shown in table 5.

TABLE 5

Therapeutic effect of VIS 707 on time to healing and cumulative score

| Treatment | Time to healing, days MEAN | S.D. | Cumulative score MEAN | S.D. |
|---|---|---|---|---|
| 5% VIS 707 ointment | 6.6 | 1.8 | 9.0 | 4.1 |
| Placebo ointment | 9.8 | 1.5 | 19.8 | 4.4 |

C. Experiments using a systemic HSV-2 infection in mice have shown that VIS 707 administered orally has a therapeutic effect. The method used has been described by Olsen et al (The Journal of Infectious Diseases Vol. 137 (1978) 428–436). Treatment started 1 hour after infection and continued for 10 days. The mice were treated by the perorally route two times daily with 75 mg/kg VIS 707 or with phosphate buffered saline as placebo. The results are shown in table 6. Treatment with VIS 707 reduced the final mortality and increased the mean day to death (MDD).

TABLE 6

Effect of treatment with VIS 707 on the mortality rate and mean day of death in mice infected i.p. with herpes simplex type 2.

| Treatment | No. dead/ /no. tested | % | Mean day to death |
|---|---|---|---|
| VIS 707 | 3/10 | (30) | 13.7 |
| Placebo | 10/10 | (100) | 9.3 |

The animal experiments showed that VIS 707 had a therapeutic effect on herpes keratitis, on cutaneous herpes infections and on systemic herpes infections as shown in tables 4, 5 and 6, respectively.

The test described in C was also conducted for R-(+)-9-(3,4-dihydroxybutyl)guanin, herebelow denoted (R)-VIS707, as follows. Comparison was made with the effect of placebo and the effect of the prior art compound acyclovir.

Female NMRI mice weighing 15.0±0.9 g were inoculated i.p. with $10^4$ PFU herpes simplex type 2 virus. They were divided into five groups with 10 mice in each group.

Two groups received (R)-VIS707 and two groups were given acyclovir. The dose 15 mg/kg bodyweight was used for both drugs.

Treatment was started one hour post inoculation and the compounds were given orally twice daily for 10 days. The untreated control group received placebo.

The mortality in the group receiving (R)-VIS707 was 30% compared to 70% mortality in the acyclovir treated group. See Table 7 below.

TABLE 7

Effect of (R)-VIS707 and acyclovir, in dose level 15 mg/kg bodyweight at oral administration, and palcebo on systemic HSV-2 infection in mice

| Test compound | Percent mortality, days after inoculation | | | | | | | |
|---|---|---|---|---|---|---|---|---|
| | 7 | 8 | 9 | 10 | 11 | 13 | 14 | 17 |
| placebo | 20 | 50 | 90 | | | | | 90 |
| acyclovir | | 10 | | 20 | 40 | 40 | 70 | 70 |
| (R)-VIS707 | | 10 | | 10 | 20 | 20 | 30 | 30 |

BEST MODE OF CARRYING OUT THE INVENTION

Among the compounds of the present invention according to formula I, the compound 9-(3,4-dihydroxybutyl)guanine and its use for the treatment of herpes virus infections represents the best mode known at present.

We claim:

1. A compound of the formula $$\text{HN-C(=O)-C=C(N=CH-)-N(H_2N-C(=N)-N-)-CH_2-CH(R_1)-CH(R_2)-CH_2OH} \quad \text{I}$$

wherein each of $R_1$ and $R_2$, which are the same or different is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; or a physiologically acceptable salt or an optical isomer thereof.

2. A compound according to claim 1; 9-(3,4-dihydroxybutyl)guanine.

3. A compound according to claim 1; 9-(2,4-dihydroxybutyl)guanine.

4. A compound according to claim 1; 9-(2,3,4-trihydroxybutyl)guanine, optionally as the erythro or threo form.

5. A compound of the formula:

$$\text{HN-C(=O)-C=C(N=CH-)-N(H_2N-C(=N)-N-)-CH_2-CH_2-CH(F)-CH_2OH}$$

or a physiologically acceptable salt or an optical isomer thereof.

6. A compound of the formula:

$$\text{HN-C(=O)-C=C(N=CH-)-N(H_2N-C(=N)-N-)-CH_2-CH(F)-CH_2-CH_2OH}$$

or a physiologically acceptable salt or an optical isomer thereof.

7. A compound of the formula:

$$\text{HN-C(=O)-C=C(N=CH-)-N(H_2N-C(=N)-N-)-CH_2-CH(F)-CH(F)-CH_2OH}$$

or a physiologically acceptable salt or an optical isomer thereof.

8. A compound according to one of claims 1, 2, 3, 4, 5, 6 or 7 in the form of an optical isomer thereof.

9. A compound according to one of claims 1, 2, 3, 4, 5, 6 or 7 in the form of a physiologically acceptable salt thereof.

10. A pharmaceutical preparation for combating herpes infections comprising as an active ingredient a compound of the formula

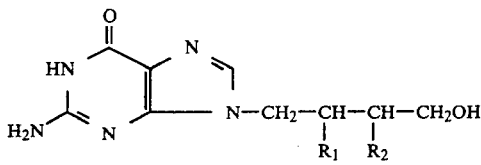

wherein each of $R_1$ and $R_2$, which are the same or different is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; or a physiologically acceptable salt or an optical isomer thereof; in conjunction with a pharmaceutically acceptable carrier.

11. A pharmaceutical preparation according to claim 10 designed for systemic administration.

12. A pharmaceutical preparation according to claim 10 designed for topical administration.

13. A method for the treatment of herpes virus infections in an animal or human host in need of treatment, comprising administering a therapeutically effective amount of a compound of the formula

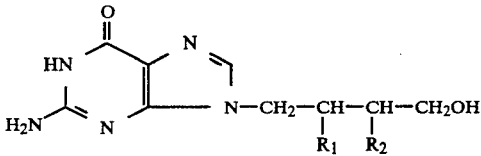

wherein each of $R_1$ and $R_2$, which are the same or different is hydrogen, hydroxy or fluoro; provided that $R_1$ or $R_2$ is hydrogen when $R_1$ and $R_2$ are different, and provided that $R_1$ and $R_2$ are hydroxy or fluoro when $R_1$ and $R_2$ are the same; or a physiologically acceptable salt or an optical isomer thereof.

14. A method according to claim 13 for the treatment of infections caused by herpesviruses.

15. R-(+)-9-(3,4-dihydroxybutyl)guanine and physiologically acceptable salts thereof.

16. A pharmaceutical preparation according to claims 10, 11 or 12, comprising R-(+)-9-(3,4-dihydroxybutyl) guanine or a physiologically acceptable salt thereof as active ingredient.

17. A method according to claim 13, comprising administering a therepeutically effective amount of R-(+)-9-(3,4-dihydroxybutyl)guanine or a physiologically acceptable salt thereof.

18. A pharmaceutical preparation according to claims 10, 11 or 12, comprising 9-(3,4-dihydroxybutyl) guanine or a physiologically acceptable salt thereof as active ingredient.

19. A pharmaceutical preparation according to claims 10, 11 or 12, comprising 9-(2,4-dihydroxybutyl) guanine or a physiologically acceptable salt thereof as active ingredient.

20. A pharmaceutical preparation according to claims 10, 11 or 12, comprising 9-(2,3,4-trihydroxybutyl) guanine or a physiologically acceptable salt thereof as active ingredient.

21. A pharmaceutical preparation according to claims 10, 11 or 12, comprising 9-(3-fluoro-4-hydroxybutyl) guanine or a physiologically acceptable salt thereof as active ingredient.

22. A pharmaceutical preparation according to claims 10, 11 or 12, comprising 9-(2-fluoro-4-hydroxybutyl) guanine or a physiologically acceptable salt thereof as active ingredient.

23. A pharmaceutical preparation according to claims 10, 11 or 12, comprising 9-(2,3-difluoro-4-hydroxybutyl) guanine or a physiologically acceptable salt thereof as active ingredient.

24. A method according to claim 13, comprising administering a therapeutically effective amount of 9-(3,4-dihydroxybutyl) guanine or a physiologically acceptable salt thereof.

25. A method according to claim 13, comprising administering a therapeutically effective amount of 9-(2,4-dihydroxybutyl) guanine or a physiologically acceptable salt thereof.

26. A method according to claim 13, comprising administering a therapeutically effective amount of 9-(2,3,4-trihydroxybutyl) guanine or a physiologically acceptable salt thereof.

27. A method according to claim 13, comprising administering a therapeutically effective amount of 9-(3-fluoro-4-hydroxybutyl) guanine or a physiologically acceptable salt thereof.

28. A method according to claim 13, comprising administering a therapeutically effective amount of 9(2-fluoro-4-hydroxybutyl) guanine or a physiologically acceptable salt thereof.

29. A method according to claim 13, comprising administering a therapeutically effective amount of 9-(2,3-difluoro-4-hydroxybutyl) guanine or a physiologically acceptable salt thereof.

30. A hydrochloride salt according to claim 1; 9-(3,4-dihydroxybutyl) guanine.

31. A hydrochloride salt according to claim 1; 9-(2,4-dihydroxybutyl) guanine.

32. A hydrochloride salt according to claim 1; 9-(2,3,4-trihydroxybutyl) guanine.

* * * * *

UNITED STATES PATENT AND TRADEMARK OFFICE
CERTIFICATE OF CORRECTION

PATENT NO. : 4,495,190

DATED : January 22, 1985

INVENTOR(S) : Hagberg et al.

It is certified that error appears in the above-identified patent and that said Letters Patent is hereby corrected as shown below:

Col. 3, line 40, "in" should read --to--;

Col. 8, to the right of the formula in lines 50-57, insert --XII--;

Col. 10, line 48, "substition" should be --substitution--;

Col. 12, line 67, "preparation" should read --preparations--;

Col. 17, line 35, "(0.38" should read --(0.33--;

Col. 18, line 34, "Example 8" should read --Example 9--;

Col. 18, line 49, "borohyride" should read --borohydride--;

Col. 20, line 42, "A. Hol" should read --A. Holy--;

Col. 21, line 15, "acid a satured" should read --acid, a saturated--;

Col. 21, line 20, "satured" should be --saturated--; and

Col. 30, line 42, "9(2" should read --9-(2--.

Signed and Sealed this

Ninth Day of July 1985

[SEAL]

Attest:

DONALD J. QUIGG

Attesting Officer    Acting Commissioner of Patents and Trademarks